US008575088B2

United States Patent
Li

(10) Patent No.: US 8,575,088 B2
(45) Date of Patent: Nov. 5, 2013

(54) METHOD OF PREVENTING ACUTE OR SUB-ACUTE HEPATIC FAILURE BY ADMINISTERING A LONG-ACTING RECOMBINANT HUMAN SOLUBLE TUMOR NECROSIS FACTOR ALPHA RECEPTOR II FUSION PROTEIN

(75) Inventor: Hai Li, Shanghai (CN)

(73) Assignee: Zhenyi Li, Shanghai (CN)

( * ) Notice: Subject to any disclaimer, the term of this patent is extended or adjusted under 35 U.S.C. 154(b) by 0 days.

(21) Appl. No.: 13/529,402

(22) Filed: Jun. 21, 2012

(65) Prior Publication Data

US 2012/0294858 A1    Nov. 22, 2012

Related U.S. Application Data

(62) Division of application No. 12/090,037, filed as application No. PCT/CN2006/002689 on Oct. 13, 2006, now Pat. No. 8,227,404.

(30) Foreign Application Priority Data

Oct. 14, 2005 (CN) .......................... 2005 1 0030570
Mar. 21, 2006 (CN) .......................... 2006 1 0071247

(51) Int. Cl.
   *A61K 38/00* (2006.01)
   *A61K 45/00* (2006.01)
   *A61K 38/16* (2006.01)
   *A61P 43/00* (2006.01)

(52) U.S. Cl.
   USPC ......... 514/1.1; 424/85.1; 424/85.2; 514/18.9; 514/21.2

(58) Field of Classification Search
   None
   See application file for complete search history.

(56) References Cited

U.S. PATENT DOCUMENTS

| 5,703,048 | A  | 12/1997 | Roos et al.    |
|-----------|----|---------|----------------|
| 6,380,164 | B1 | 4/2002  | Oeltgen et al. |
| 6,541,610 | B1 | 4/2003  | Smith          |
| 6,559,168 | B2 | 5/2003  | Marfat et al.  |
| 7,144,987 | B1 | 12/2006 | Chirino et al. |
| 7,238,660 | B2 | 7/2007  | Rosen et al.   |
| 7,276,477 | B2 * | 10/2007 | Osslund et al. ............ 514/16.6 |
| 8,101,178 | B2 * | 1/2012  | Babcook et al. ........... 424/133.1 |
| 2003/0124105 | A1 | 7/2003 | Yuan et al. |
| 2005/0020656 | A1 | 1/2005 | Horie et al. |

FOREIGN PATENT DOCUMENTS

| CN | 1240479     | 1/2000 |
| CN | 1408875     | 4/2003 |
| WO | 2004/060911 | 7/2004 |

OTHER PUBLICATIONS

Fang et al., "Activation of the tumor necrosis factor-alpha system in the liver in chronic hepatitis B virus infection" Am J Gastroenterol 1996; vol. 91, No. 4, pp. 748-753.
Song et al. "Tumor necrosis factor-alpha induces apoptosis of enterocytes in mice with fulminant hepatic failure", World J Gastroenterol, 2005; vol. 11, No. 24, pp. 3701-3709.
Kallinowski et al. "Induction of tumor necrosis factor (TNF) receptor type p55 and p75 in patients with chronic hepatitis C virus (HCV) infection," Clin Exp Immunol. 1998; No. 111, pp. 269-277.
Gu, Qiuhong, "Expression of TNFR1 in fulminant hepatic failure of mice induced by LPS and GaIN" China Medical University, Master's Theses, Jul. 20, 2004, 35 pages.
Ding, Shihua, "The relationship between inerleukin-10, interleukin-18, soluble tumor necrosis factor receptor and hepatitis B-associated chronic liver," Medicines, Jiangxi Oct. 15, 2004, 28 pages.

* cited by examiner

*Primary Examiner* — Robert Landsman
(74) *Attorney, Agent, or Firm* — Hamre, Schumann, Mueller & Larson, P.C.

(57) ABSTRACT

The present invention belongs to the field of the application of genetic engineering and gene function, and it is directed to a new medical use of the gene encoding the recombinant soluble tumor necrosis factor α receptor (HusTNFR). The present invention made intervention to fulminant hepatic failure in mice by use of the long-acting recombinant human soluble tumor necrosis factor αreceptor and the classic animal models of acute and sub-acute hepatic failure. The results showed that the long-acting soluble tumor necrosis factor αreceptor of the present invention has a half-life extended more than 10 times, and it significantly decreased the mortality of model animals and has superior therapeutic effect for the treatment and/or prophylaxis of acute and sub-acute hepatic failure in model animals. These receptors have a noticeable therapeutic effect for the treatment and/or prophylaxis of acute and sub-acute hepatic failure in comparison with the non-long-acting HusTNFR.

5 Claims, No Drawings

METHOD OF PREVENTING ACUTE OR SUB-ACUTE HEPATIC FAILURE BY ADMINISTERING A LONG-ACTING RECOMBINANT HUMAN SOLUBLE TUMOR NECROSIS FACTOR ALPHA RECEPTOR II FUSION PROTEIN

CROSS-REFERENCE TO RELATED APPLICATIONS

This application is a Division of application Ser. No. 12/090,037, filed Apr. 11, 2008, which is a US National Stage Application of PCT/ CN2006/002689, filed Oct. 13, 2006, which applications are incorporated herein by reference. Application Ser. No. 12/090,037 is now U.S. Pat. No. 8,227, 404.

TECHNICAL FIELD

The present invention belongs to the field of the application of genetic engineering and gene function. Particularly, it relates to a new medical use of the gene encoding the recombinant soluble tumor necrosis factor αreceptor (HusTNFR), and more particularly, it relates to use of the long-acting recombinant human soluble tumor necrosis factor α receptor (LHusTNFR) in the treatment and/or prophylaxis of acute and sub-acute hepatic failure.

BACKGROUND ART

Fulminant hepatic failure (FHF) is a syndrome defined as necrosis of a large number of liver cells or severe impairment of liver function and hepatic encephalopathy within 8 weeks after the initial symptom or within 10 days of the on-set of jaundice in the absence of previous liver disease. It is characterized by rapid on-set, severe condition, absence of effective treatment and high mortality.

The acute inflammation and necrosis of liver cells may lead to two different diseases: acute hepatitis and fulminant hepatic failure (also called acute hepatic failure). Acute hepatitis caused by hepatitis virus is referred to as acute viral hepatitis, and the acute hepatitis caused by alcohol is called as acute alcoholic hepatitis. Although necrosis of liver cells is widely seen in all kinds of hepatitis described above, the necrosis is not so severe to lead to hepatic dysfunction. FHF is distinguished from various acute hepatitis in that awfully rapid necrosis of liver cells happens in FHF, resulting in hepatic failure due to dysfunction of the remaining normal hepatocytes, and eventually leading to extremely high mortality.

The leading cause of FHF in China is hepatitis virus infection, while other causes including medical or poison toxicosis, ischemia and anoxia, metabolic disorder, and autoimmune hepatitis, etc. Currently no medicaments are available to specifically block the acute necrosis of liver cells, and thus hepatic failure due to large quantities of hepatic cell necrosis cannot be prevented. As a result, it keeps ongoing difficult to reduce the mortality of FHF, and there is an urgent clinical need for a medicament capable of specifically and rapidly preventing acute hepatic cell necrosis, thereby treating hepatic failure.

Recent studies have revealed that binding of TNFα and its receptor is the first pathway to trigger hepatic cell necrosis, which plays an important role in the mechanism of hepatocyte impairment. Blocking said binding will block the starting point of hepatic cell necrosis, whereby enabling the pharmaceutical treatment of FHF.

At present, there are two classes of TNFαinhibitor that directly interrupt the binding of TNFαand its receptor: monoclonal antibody against TNFα, and soluble TNFα receptor analogue. These TNFαinhibitors, which bind TNFαin vivo, will theoretically prevent the binding of TNFα in blood or intercellular fluid to its receptor on the membrane of hepatocytes, thereby preventing the activation of the cell necrosis pathway.

Recent studies found that monoclonal antibody of TNFα is not a suitable candidate medicament due to its characteristic of activating TNFα on cell membrane which leads to apoptosis of the target cells, in addition to its ability to block the binding of TNFαto TNFα receptor type I.

The conventional soluble TNFαreceptors can to some extent decrease the mortality in the most animal models of mild hepatic cell necrosis and acute hepatitis; however, it cannot effectively decrease the mortality of acute or sub-acute hepatic failure caused by massive hepatocyte necrosis. Furthermore, the reason of the poor therapeutic effect is still not known so far by those of the skill in the art. Consequently, it is still difficult now for the soluble TNFα receptors to find their use practically in clinical applications to treat massive hepatocytes necrosis or hepatic failure.

In summary, there is an earnest demand in the art to find the reason for the poor therapeutic effect of TNFαreceptors for treating hepatic cell necrosis, so as to modify the TNFαreceptors to confer it the ability to effectively and rapidly prevent the occurrence of extensive acute necrosis of hepatocytes, and thereby making it a superior medicament for clinically treating and preventing acute and sub-acute hepatic failure.

Contents of the Invention

In the first aspect, the present invention provides a use of long-acting soluble tumor necrosis factor αreceptor in the manufacture of a medicament for the treatment and/or prophylaxis of hepatocyte necrosis or hepatic failure.

In a preferred embodiment, the long-acting soluble tumor necrosis factor αreceptor is a long-acting recombinant human soluble tumor necrosis factor αreceptor.

In a further preferred embodiment, the long-acting soluble tumor necrosis factor α receptor has a half-life of 12-140 hours (preferably, 24-72 hours).

In a further preferred embodiment, the long-acting soluble tumor necrosis factor α receptor is selected from the group consisting of:

a. a fusion protein of human tumor necrosis factor αreceptor type I with human IgG1:Fc fragment (preferably, the carboxyl terminal of the human tumor necrosis factor αreceptor type I being linked to the amino terminal of the IgG1:Fc fragment), b. a fusion protein of human tumor necrosis factor αreceptor type II with human IgG1:Fc fragment (preferably, the carboxyl terminal of the human tumor necrosis factor α receptor type II being linked to the amino terminal of the IgG1:Fc fragment), c. a human tumor necrosis factor αreceptor type I protein PEGylated at the amino terminal, d. a human tumor necrosis factor αreceptor type I protein PEGylated at the carboxyl terminal, e. a human tumor necrosis factor αreceptor type II protein PEGylated at the amino terminal, f. a human tumor necrosis factor αreceptor type II protein PEGylated at the carboxyl terminal, h. a human tumor necrosis factor αreceptor type I protein embedded in a PEG-liposome mixture, i. a human tumor necrosis factor α receptor type II protein embedded in a PEG-liposome mixture, j. a fusion protein of human tumor necrosis factor αreceptor type I with human serum albumin, or k. a fusion protein of human tumor necrosis factor αreceptor type II with human serum albumin.

In a further preferred embodiment, the long-acting soluble tumor necrosis factor α receptor decreases the IL-6 level in hepatocytes by 40-50%;

decreases the MIP-2 level in hepatocytes by 50-60%;

decreases the bcl-xl level in hepatocytes by 30-45%; or decreases the NF-κB level in hepatocytes by 30-45%.

In a further preferred embodiment, the hepatic failure is acute and/or sub-acute hepatic failure.

In a further preferred embodiment, the hepatocyte necrosis is massive hepatocyte necrosis.

In a further preferred embodiment, the hepatocyte necrosis is acute massive hepatocyte necrosis.

In the second aspect, the present invention provides a pharmaceutical composition comprising:

(i) an effective amount (for example, 0.00001-50wt %; more preferably, 0.0001-20wt %; the most preferably, 0.001-10wt %) of a long-acting soluble tumor necrosis factor αreceptor selected from the group consisting of:

a. a fusion protein of human tumor necrosis factor αreceptor type I with human IgG1:Fc fragment (preferably, the carboxyl terminal of the human tumor necrosis factor αreceptor type I being linked to the amino terminal of the IgG1:Fc fragment), b. a fusion protein of human tumor necrosis factor αreceptor type II with human IgG1:Fc fragment (preferably, the carboxyl terminal of the human tumor necrosis factor α receptor type II being linked to the amino terminal of the IgG1:Fc fragment), c. a human tumor necrosis factor αreceptor type I protein PEGylated at the amino terminal, d. a human tumor necrosis factor αreceptor type I protein PEGylated at the carboxyl terminal, e. a human tumor necrosis factor αreceptor type II protein PEGylated at the amino terminal, f. a human tumor necrosis factor αreceptor type II protein PEGylated at the carboxyl terminal, h. a human tumor necrosis factor αreceptor type I protein embedded in a PEG-liposome mixture, i. a human tumor necrosis factor α receptor type II protein embedded in a PEG-liposome mixture, j. a fusion protein of human tumor necrosis factor αreceptor type I with human serum albumin, or k. a fusion protein of human tumor necrosis factor αreceptor type II with human serum albumin; and (ii) a pharmaceutically acceptable vehicle.

In a further preferred embodiment, the pharmaceutical composition further comprises an effective amount (for example, 0.00001-50wt %; more preferably, 0.0001-20wt %; the most preferably, 0.001-10wt %) of one or more agents selected from the group consisting of:

(iii) human hepatocyte growth factor (huHGF), reduced glutathione and matrine.

In the third aspect, the present invention provides a method of treating or preventing the hepatocyte necrosis or the hepatic failure, comprising the step of administering to a subject in need of such a treatment an effective amount (for example, 0.00001-50wt %; more preferably, 0.0001-20wt %; the most preferably, 0.001-10wt %) of a long-acting soluble tumor necrosis factor αreceptor.

In a preferred embodiment, the long-acting soluble tumor necrosis factor αreceptor is selected from the group consisting of:

a. a fusion protein of human tumor necrosis factor αreceptor type I with human IgG1:Fc fragment (preferably, the carboxyl terminal of the human tumor necrosis factor αreceptor type 1 being linked to the amino terminal of the IgG1:Fc fragment), b. a fusion protein of human tumor necrosis factor αreceptor type II with human IgG1:Fc fragment (preferably, the carboxyl terminal of the human tumor necrosis factor α receptor type II being linked to the amino terminal of the IgG1:Fc fragment), c. a human tumor necrosis factor αreceptor type I protein PEGylated at the amino terminal, d. a human tumor necrosis factor αreceptor type I protein PEGylated at the carboxyl terminal, e. a human tumor necrosis factor αreceptor type II protein PEGylated at the amino terminal, f. a human tumor necrosis factor αreceptor type II protein PEGylated at the carboxyl terminal, h. a human tumor necrosis factor αreceptor type I protein embedded in a PEG-liposome mixture, i. a human tumor necrosis factor α receptor type II protein embedded in a PEG-liposome mixture, j. a fusion protein of human tumor necrosis factor αreceptor type I with human serum albumin, or k. a fusion protein of human tumor necrosis factor αreceptor type II with human serum albumin;

In a preferred embodiment, the hepatic failure is acute and/or sub-acute hepatic failure.

MODE OF CARRYING OUT THE INVENTION

Inventors of the present invention, through a persistent and extensive investigation and experiments, has found for the first time that the continuous and consistent block on the activity of hepatocytes induced by the soluble TNFαreceptor is important to the treatment and/or prevention of acute massive hepatocytic necrosis. That is, it is required to maintain a stable and persistent level of soluble TNFαreceptor in blood and liver. In contrast, conventional TNFαreceptor, which has a short-time and pulse-moded action, is sufficient for the mild hepatocyte necrosis in acute hepatitis. Thus, inventors of the present invention discovered the reason why the conventional soluble TNF α receptor cannot effectively prevent acute massive hepatocyte necrosis in acute hepatic failure. It is believed that its short half-life and instability in vivo prevent it from providing a stable and sustained action against hepatocyte necrosis. Then, inventors of the present invention have modified the TNF αreceptor in different manners to prolong the acting time of TNFαreceptor in its active form in vivo and thus to produce long-acting TNFαreceptors that can provide a stable and sustained therapeutic effect. These modifications improved the effect of TNFαreceptors in treating and preventing acute hepatocyte necrosis. Further, it is the first time that modified TNFαreceptors were used in treating acute and sub-acute hepatic failures. These constitute the basis of the present invention.

As used herein, the term "a long-acting soluble tumor necrosis factor αreceptor" refers to a tumor necrosis factor α receptor having an prolonged half-life (that is, it can be maintained at an effective concentration for a longer time in vivo). Generally, "a long-acting soluble tumor necrosis factor αreceptor" has a half-life of more than 12 hours (e.g. 12-140 hrs). Various methods can be employed to extend the half-life of tumor necrosis factor α receptor, including but not limited to, fusion of the tumor necrosis factor αreceptor with the human IgG1:Fc fragment, PEGylation of the tumor necrosis factor αreceptor, embedment of the tumor necrosis factor αreceptor within a PEG-liposome mixture and fusion of the tumor necrosis factor α receptor with the human serum albumin. Preferably, the "long-acting soluble tumor necrosis factor α receptor" is a "long-acting recombinant human soluble tumor necrosis factor αreceptor".

One object of the present invention is to provide a new pharmaceutical use of the gene of recombinant soluble tumor necrosis factor αreceptor (HusTNFR), particularly a new use of the gene encoding recombinant soluble tumor necrosis factor αreceptor (HusTNFR) or the long-acting modified recombinant human soluble tumor necrosis factor α receptor (LHusTNFR) in prevention and/or treatment of acute and sub-acute hepatic failure.

A further object of the present invention is to provide a medicament that more significantly decrease the mortality of hepatic failure than conventional soluble tumor necrosis factor αreceptors. This object is mainly achieved by increasing the half-life of the soluble tumor necrosis factor αreceptor-based agent to prolong its time of action, and thereby improving the therapeutic efficacy.

The present invention intervened the fulminant hepatic failure with long-acting recombinant human soluble tumor necrosis factor αreceptors in classic acute and sub-acute hepatic failure models in mouse. The results showed that the death rates in the intervention group and the model group (without intervention) were 0% and 80%, respectively.

The above-said tumor necrosis factor (TNF) may be tumor necrosis factor α, which binds to a recombinant long-acting soluble protein of the corresponding receptor on the cell membrane. The said recombinant long-acting soluble protein of the receptor may be, for example, a long-acting recombinant human soluble tumor necrosis factor αreceptor type I (LHusTNFRI) or a long-acting recombinant human soluble tumor necrosis factor αreceptor type II (LHusTNFRII), which has a half-life 10 times longer than a normal recombinant human soluble tumor necrosis factor αreceptor type I (HusTNFRI) and recombinant human soluble tumor necrosis factor α receptor type II (HusTNFRI), respectively. These recombinant receptors may be in the form of: (1) HusTNFRI or HusTNFRII with the carboxyl terminal linked to human immunoglobulin IgG:Fc fragment, or (2) HusTNFRI or HusTNFRII with the amino terminal linked to PEG, or (3) HusTNFRI or HusTNFRII encapsulated in PEG-liposome, or (4) HusTNFRI or HusTNFRII with the carboxyl or amino terminal linked to human serum albumin. Said LHusTNFRI and LHusTNFRII are significantly more effective than HusTNFRI or HusTNFRII in the treatment and/or the prophylaxis of acute or sub-acute hepatic failure.

The animal model of acute or sub-acute hepatic failure may be established by administering D-aminogalactose and endotoxin to rats or mice) via endodermic injection. Such an animal model has a high mortality of 60-80% due to hepatic failure.

The long-acting recombinant human soluble tumor necrosis factor α receptor (LHusTNFR) according to the present invention may be produced in the form of:
  a. a recombinant protein expressed from a fusion gene of the gene encoding human TNF αreceptor (TNFR) type I and the gene encoding human IgG1:Fc fragment,
  b. a recombinant protein expressed from a fusion gene of the gene encoding human TNF αreceptor (TNFR) type II and the gene encoding human IgG1:Fc fragment,
  c. a human tumor necrosis factor αreceptor type I protein PEGylated at the amino terminal,
  d. a human tumor necrosis factor αreceptor type I protein PEGylated at the carboxyl terminal,
  e. a human tumor necrosis factor αreceptor type II protein PEGylated at the amino terminal,
  f. a human tumor necrosis factor αreceptor type II protein PEGylated at the carboxyl terminal,
  h. a human tumor necrosis factor αreceptor type I protein embedded in a PEG-liposome mixture,
  i. a human tumor necrosis factor α receptor type II protein embedded in a PEG-liposome mixture,
  j. a fusion protein of a human tumor necrosis factor αreceptor type I with human serum albumin, or
  k. a fusion protein of human tumor necrosis factor αreceptor type II with human serum albumin.

The long-acting recombinant human soluble tumor necrosis factor α receptor (LHusTNFR) according to the present invention, when administered to mice with D-aminogalactose and endotoxin-induced acute hepatic failure (herein after, referred to as "acute hepatic failure animal(s)") in a prophylaxis test, decreased the mortality due to acute hepatic failure from 80% to 0%. The long-acting recombinant human soluble tumor necrosis factor α receptor (LHusTNFR) according to the present invention, when administered to rats with D-aminogalactose and endotoxin-induced sub-acute hepatic failure (herein after, reffered to as "sub-acute hepatic failure animal(s)") in the prophylaxis and treatment tests, decreased the mortality due to sub-acute hepatic failure animal from 80% to 0%. These results show that the long-acting recombinant human soluble tumor necrosis factor α receptors of type I and type II, which have a longer half-life, can significantly decrease the mortality in model animals, have excellent therapeutic effect in treatment and/or prophylaxis of acute and sub-acute hepatic failure, and are thus therapeutically and prophylactically effective against acute and sub-acute hepatic failure. More over, such findings may lead to a development of a novel medicament to significantly reduce the mortality due to acute hepatic failure.

According to the present invention,
(1) A gene encoding the LHusTNFR type I as set forth in SEQ ID NO: 1 is prepared. The method of preparation comprises the steps of cloning the gene encoding the extra-membrane amino acids of the sTNFR (human) type I (i.e., amino acids 1-171 of SEQ ID NO: 1) and the gene encoding the Fc fragment of the of human immunoglobulin γ1 (IgG1:Fc) (i.e., amino acid positions 172-403 of SEQ ID NO: 1), preferably into an appropriate plasmid; identifying and screening for positive clones harboring the fusion of type I TNFR-IgG1:Fc fragment through DNA restriction enzyme digestion; and confirming the target genes via nucleotide sequencing.

(2) A gene encoding the LHusTNFR type II as set forth in SEQ ID NO: 2 is prepared. The preparation comprises the steps of cloning the gene ecoding the extra-membrane amino acids of the sTNFR (human) type II (i.e. amino acids 1-235 of SEQ ID NO: 2) and the gene ecoding the Fc fragment of the of human immunoglobulin γ1 (IgG1:Fc) (i.e. amino acids 236-467 of SEQ ID NO: 2) into an appropriate plasmid, identifying and screening for the positive clones harboring the fusion of type II TNFR-IgG1:Fc fragment through DNA restriction enzyme digestion, and confirming the target genes via nucleotid sequencing.

The obtained cDNA fragment of TNFR (I or II)-IgG1:Fe may be cloned into an expression vector to form a recombinant expression vector such as a plasmid. According to the present invention, there is no specifict limites on the expression plasmid. In a preferred embodiment, a prokaryotic expression vector, for example, pET28, is used.

The obtained expression vector may be introduced to an appropriate host cell using any suitable conventional methods. The present invention is not limited to any specific host cells. Any host, as long as it allows the expression of the recombinant expression vector, may be used. In a preferred embodiment, the Brewer's yeast, BL21 is used.

The expression product according to the present invention is secreted as inclusion bodies in the cytoplasm of host cells. The inclusion bodies may be isolated from the lysate of the host cells, and then lysed with high concentration of urea or guanidine hydrochloride. The LHusTNFR is purified from the lysate of the inclusion bodies, and then renatured to give the active LHusTNFR (type I or II)-IgG1:Fc.

All the operations in molecular biology are carried out according to "Molecular cloning: a laboratory manual" (Sambrook and D. W. Russell, New York: Cold Spring Harbor Laboratory Press).

(3) The cDNA encoding the extra-membrane amino acids of sTNFR (human) type I (i.e., amino acids 1-171 of SEQ ID NO: 1) is cloned into a expression vector to produce a recombinant expression plasmid (SEQ ID NO: 3)

The present invention is not limited to any specific expression plasmids. In a preferred embodiment, a prokaryotic expression vector, for example, pET28, is used.

The said recombinant expression vector may be introduced into an appropriate host cells as previously taught. The present invention is not limited to any specific host cells. Any host cells, as long as it allows the expression of the recombinant expression vectors can be used. In a preferred embodiment, E. coli BL21 is employed. The expression product according to the present invention is secreted as inclusion bodies in the cytoplasm of the host cells. The inclusion bodies may be isolated from the lysate of the host cells, and then lysed with high concentration of urea or guanidine hydrochloride. The LHusTNFR type I is purified from the lysate of the inclusion bodies, and then renatured to give the active LHusTNFR type I.

Active mPEG(s) of molecular weight (MW) no less than 20,000 may be coupled to the amino terminal or the carboxyl terminal of HusTNFR type I. The present invention is not limited to any specific mPEG molecules. In a preferred embodiment, mPEG2-ALD of MW 40,000 from Shearwater corporation (New Jersey, USA) was coupled to the amino terminal of HusTNFR type I. And, in another embodiment, an mPEG2-NHS easter of MW 40,000 from Shearwater corporation (New Jersey, USA) was coupled to the carboxyl terminal of HusTNFR type I.

The reaction can be expressed by the formula:

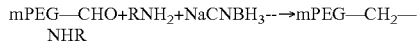

The reaction condition includes pH 7.9 and a duration of 12 hrs.

(4) The cDNA encoding the extra-membrane amino acids 1-235 of sTNFR (human) type II is cloned into an expression vector to produce a recombinant expression plasmid (SEQ ID NO: 4).

The present invention is not limited to any specific expression plasmids. In a preferred embodiment, a prokaryotic expression vector, for example, pET28, was used.

The said recombinant expression vector may be introduced into an appropriate host cells as previously taught. The present invention is not limited to any specific host cells. Any host cells, as long as it allows the expression of the recombinant expression vectors can be used. In a preferred embodiment, E. coli BL21 was used. The expression product according to the present invention is secreted as inclusion bodies into the cytoplasm of host cells. The inclusion bodies may be isolated from the lysate of the host cells, and then lysed with high concentration of urea or guanidine hydrochloride. The LHusTNFR type II is purified from the lysate of the inclusion bodies, and then renatured to give the active LHusTNFR type II.

Active mPEG(s) with a molecular weight (MW) of no less than 20,000 may be coupled to the amino or the carboxyl terminal of HusTNFR type II. The present invention is not limited to any specific mPEG molecules. In a preferred embodiment, mPEG2-ALD of MW 40,000 from Shearwater corporation (New Jersey, USA) was coupled to the amino terminal of HusTNFR type II. And in another embodiment, an mPEG2-NHS easter of MW 40,000 (Shearwater corporation, New Jersey, USA) was coupled to the carboxyl terminal of HusTNFR type II.

The reaction may be expressed by the formula:

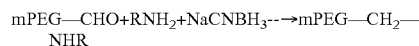

The reaction condition includes pH 7.9 and a duration of 12 hrs.

(5) The HusTNFR type I or the HusTNFR type II is encapsulated with the long circulating liposome-polyethylene glycol-derived phospholipid to produce the long-acting HusTNFR type I or type II.

DOPE-PEG-MAL (WM 4108.04) is produced by reacting dioleoyl-phosphatidylethanolamine (DOPE) (WM 744.04, Aanti Polar Lipids, U.S.A.), NHS-PEG$_{3540}$-MAL (Nhydroxysulfosuccinimide-polyoxyethylene (MW 3540)-maleimide) (MW 3477, Aanti Polar Lipids, U.S.A.) and TEA in a molar ratio of 1:1:0.1 in the presence of triethylamine as the catalyst at 25° C. for 6 hrs and then subjecting the resultant to centrifugation, evaporation and vacuum dehydration.

Then, the long circulating liposome-polyethylene glycol-derived phospholipid is produced by reacting the obtained DOPE-PEG-MAL, EPC(L-α-Phosphatidylcholine, MW 760.09, cholesterol (MW 386.67), and mPEG-2000-DOPE (MW 2801.51) (Aanti Polar Lipids, U.S.A.) at a molar ratio of 200:20:10:1 in chloroform in a water bath at 40° C., and then rotary evaporating at 100-150 r/min to remove the organic solvents, adding PBS (PH 7.4) to allow complete hydration at room temperature, extruding repeatedly with Mini Extruder, and passing through 100 nm filter for 15 times.

Finally, the long-acting HusTNFR type I or type II is obtained by adding HusTNFR type I (SEQ ID NO:3) or HusTNFR type II (SEQ ID NO:4) in PBS to the PBS solution of the obtained long circulating liposome-polyethylene glycol-derived phospholipid, oscillating at 4° C. for 30 min, and passing through CL-4B (Pharmacia, USA) to remove encapsulated HusTNFR type I or HusTNFR type II.

(6) A gene encoding LHusTNFR type I as set forth in SEQ ID NO: 5 is prepared. The method of preparatiom comprises: cloning the encoding the extra-membrane amino acids of sTNFR (human) type I (i.e. amino acids 1-171 of SEQ ID NO: 5), G(n)S-linker (i.e. amino acids 172-181) and the gene encoding human serum albumin (i.e. amino acids 182-790 of SEQ ID NO: 5) into an appropriate plasmid, identifying and screening for the positive clones harboring the fused fragment of type I TNFR-human serum albumin by DNA restriction enzyme digestion, and confirming the target gene by nucleotide sequencing.

(7) A gene encoding LHusTNFR type II as set forth in SEQ ID NO: 6 is prepared. The method of preparation comprises: cloning the gene encoding the extra-membrane amino acids of sTNFR (human) type II (i.e. amino acids 1-235 of SEQ ID NO: 2), G(n)S-linker (i.e. amino acids 236-245) and the gene encoding human serum albumin (i.e. amino acida 246-854 of SEQ ID NO: 6) into an appropriate plasmid, identifying and screening for the positive clones harboring the fused fragment of type II TNFR-human serum albumin by DNA restriction enzyme digestion, and verifying the target gene by nucleotide sequencing.

The fused cDNA fragments encoding the type I TNF αreceptor-human serum albumin and type II TNF αreceptor-human serum albumin are cloned into expression vectors, respectively, to form recombinant expression vectors. The present invention is not limited to any specific expression plasmids. In a preferred embodiment, eukaryotic expression vectors used in yeast, for example, Brewer's yeast or pichia yeast, is used.

The obtained expression vectors may be introduced into appropriate host cells as previously taught. The present invention is not limited to any specific host cells. Any host cells, as long as is allow as the expression of the recombinant expression vectors, can be used. In a preferred embodiment, the Brewer's yeast BL21 is used.

The expression product according to the present invention is secreted as inclusion bodies into the cytoplasm of the host cells. The inclusion bodies may be isolated from the lysate of the host cells, and then lysed with high concentration of urea or guanidine hydrochloride. The LHusTNFR is purified from the lysate of the inclusion bodies, and then renaturated to give the active LHusTNFR.

All the operations in molecular biology are carried out according to the "Molecular cloning: A laboratory manual" (Sambrook and D. W. Russell, New York: Cold Spring Harbor Laboratory Press).

As can be measured, the HusTNFR-IgG type I: and type II:Fc fusion proteins are maintained at effective levels in vivo for 70 to 90 hrs (i.e., a half-life of 35 to 40 hrs). The fusion protein of HusTNFR type II-human serum albumin can be maintained at effective levels in vivo for about 60 hrs (i.e., a half-life of about 30 hrs). The PEG-HusTNFR and the HusTNFR encapsuled within the long circulating liposome-polyethylene glycol-derived phospholipid can be maintained at effective levels in vivo for 6 to 11 days (i.e., a half-life of 3 to 5.5 days).

It can be seen that all the LHusTNFRs produced in different forms according to methods described above each have a half-life of more than 12 hrs (12 to 140 hrs), and hence meet the criterion of long-action. In contrast, the normal soluble tumor necrosis factor a receptor has a half-life of only 50 minutes to 2 hours.

LHusTNFR prepared by the genetic engineering method according to the present invention can efficiently prevent and treat the acute and the sub-acute hepatic failure. Comparison of properties with the conventional HusTNFR shows that the LHusTNFR has a significantly prolonged half-life and a notable improvement in the effect of preventing and/or treating the acute and the sub-acute hepatic failure and decreasing associated mortality.

The present invention further provides a pharmaceutical composition for treating the hepatocyte necrosis or the hepatic failure, which comprises the long-acting soluble tumor necrosis factor α receptor described above and a pharmaceutically acceptable vehicle. Generally, the composition is formulated in an atoxic, inert and pharmaceutically acceptable aqueous medium, wherein the pH value may be adjusted depending on the nature of the components in the formulation and/or the condition to be treated, and is typically about 5-8, preferably about 6-8. The formulated pharmaceutical composition can be administered in any suitable ways, including but not limited to intraperitoneal, intravenous or topical routes.

The composition according to the present invention may be directly used to treat hepatocyte necrosis or hepatic failure. Also, the composition may be administered in combination with other therapeutic agents such as the human hepatocyte growth factor (huHGF), the reduced glutathione and matrine, etc.

The pharmaceutical composition according to the present invention comprises a safe and effective amount of the long-acting soluble tumor necrosis factor αreceptor according to the present invention and a pharmaceutically acceptable vehicle or excipient. The said vehicle may be but not limited to a saline solution, a buffer, glucose, water, glycerin, ethanol, and a mixture thereof. The pharmaceutical composition may be formulated into appropriate forms suitable for the intended administration routes. The pharmaceutical composition according to the present invention may be in thea form suitable for injection, which may be prepared in saline or an aqueous solution comprising glucose and other excipients. The pharmaceutical composition, such as an injectable formulation or a solution, is preferably prepared under a sterile condition. The amount of active ingredients to be administered depends on the therapeutically effective amount. For example, the amount of administration may be about 0.1 microgram/kilogram body weight/day to 5 milligram/kilogram body weight/day.

When the pharmaceutical composition is used, a safe and effective amount of the long-acting soluble tumor necrosis factor αreceptor according to the present invention is administered to a mammal. Typically, the said safe and effective amount is at least about 1 microgram/kilogram body weight, while not exceeding 8 microgram/kilogram body weight in most cases. Preferably, the said safe and effective amount is about 10 microgram/kilogram body weight to about 1 milligram/kilogram body weight. Obviously, the specific dosage can readily be determined by a physician according to the factors such as the administration route and the physical condition of the patient.

The present invention will be further illustrated with the following examples. It should be understood that, these examples are exemplary only and are not intended to limit the scope of the present invention. The experimental methods in the following examples not indicating the specific experimental conditions are typically carried out under the conventional conditions, for example, those in Sambrook, et al. Molecular cloning: A laboratory manual (New York: Cold Spring Harbor Laboratory Press, 1989), or following the manufacture's instructions.

EXAMPLE 1

Prevention of Acute (Fulminant) Hepatic Failure in Mice Using Long-acting Recombinant Human Soluble Tumor Necrosis Factor (TNF) α Receptor (LHusTNFR) Type I in the Form of HusTNFR Type I-IgG1:Fc Fulminant hepatic failure was induced via subcutaneous injection of either D-aminogalactose/endotoxin (GaIN/LPS) or Con-A (T cell mitogens concanavalin A) in mice. The mortality measure after 48 hrs was 80% and 50%, respectively. The gross specimen of liver exhibited severe congestion and intumesce. The HE-staining of the pathological section showed massive severe hepatocyte necrosis.

In the group of prevention using the long-acting receptor of type I, C57BL/6 mice (GaIN/LPS sub-group) and BALB/c mice (Con-A sub-group) were subcutaneously injected with 12.5 mg/kg of the LHusTNFR type I prepared as described above (i.e., the fusion protein of LHusTNFR-IgG1 type I:Fc prepared according to the method in paragraph (1) above, used as a prophylactic agent). The C57BL/6 mice (GaIN/LPS sub-group)and the BALB/c mice (Con-A sub-group) in the group of prevention using the conventional receptor of type I were subcutaneously injected with 12.5 mg/kg of the conventional HusTNFR. The same animals in the control group were subcutaneously injected with saline at the same volume. 16 hrs later, the prevention groups and the control group were subcutaneously injected with GaIN/LPS or Con-A. The mortality after 48 hrs was observed to be 80% in the GaIN/LPS sub-group in the control group (50% in the Con-A sub-group), 50% in the prevention group using the conventional receptor type I (30% for Con-A sub-group), 0% for prevention group using the long-acting receptor of type I (0% for Con-A sub-group). In the prevention group using the long-acting receptor of type I, the pathology examination showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type I (GaIN/LPS sub-group) were decreased by 82.3%, 78.1% and 84.3% as compared with the control goup, and 44%, 52.2% and 37.8% as compared with the prevention group using the conventional receptor of type I. And, the NF-kB level was decreased by 87.4% and 37.5% respectively in the comparison. The above results indicate that the soluble TNFαreceptor type I can block the signaling to the nucleus mediated by TNFα binding to the type I receptor on the hepatic cell membrane by inhibiting the binding of TNFαto the membrane receptor, and thus prevent the hepatocytic necrosis and the necrosis-associated acute hepatic failure. The results also indicate that the long-acting soluble TNFα receptor type I has a significantly improved effect in the prevention of acute hepatic failure as compared with the conventional soluble TNFα receptor type I.

EXAMPLE 2

Prevention of Acute (Fulminant) Hepatic Failure in Mice Using Long-acting Recombinant Human Soluble Tumor Necrosis Factor (TNF) α Receptor (LHusTNFR) Type II in the Form of HusTNFR Type II -IgG1:Fc Fulminant hepatic failure was induced via subcutaneous injection of either D-aminogalactose/endotoxin (GaIN/LPS) or Con-A (T cell mitogens concanavalin A) in mice. The mortality measure after 48 hrs was 80% and 50%, respectively. The gross specimen of liver exhibited severe congestion and intumesce. The HE-staining of the pathological section showed massive severe hepatocyte necrosis.

In the group of prevention using the long-acting receptor of type II, C57BL/6 mice (GaIN/LPS sub-group) and BALB/c mice (Con-A sub-group) were subcutaneously injected with 12.5 mg/kg of the LHusTNFR type II prepared as described above (i.e., the fusion protein of LHusTNFR type II-IgG1:Fc prepared according to the method in paragraph (2) above, used as a prophylactic agent). The C57BL/6 mice (GaIN/LPS sub-group) and the BALB/c mice (Con-A sub-group) in the group of prevention using the conventional receptor of type II were subcutaneously injected with 12.5 mg/kg of the conventional HusTNFR. The same animals in the control group were subcutaneously injected with saline at the same volume. 16 hrs later, the prevention groups and the control group were subcutaneously injected with GaIN/LPS or Con-A. The mortality after 48 hrs was observed to be 80% in the GaIN/LPS sub-group in the control group (50% in the Con-A sub-group), 50% in the prevention group using the conventional receptor type II (30% for Con-A sub-group), 0% for prevention group using the long-acting receptor of type II (0% for Con-A sub-group). In the prevention group using the long-acting receptor of type II, the pathology examination showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type II (GaIN/LPS sub-group) were decreased by 78,3%, 72.1%, and 77.3%, as compared with the control group, and 44%, 52.2% and 37.8% as compared with the prevention group using the conventional receptor type II. And, the NF-kB level was decreased by 78.4% and 37.5% respectively in the comparison. The above results indicate that the soluble TNFαreceptor type II can block the signaling to the nucleus mediated by TNFα binding to the type II receptor on the hepatic cell membrane by inhibiting the binding of TNFαto the membrane receptor, and thus prevent the hepatocytic necrosis and the necrosis-associated acute hepatic failure. The results also indicate that the long-acting soluble TNFα receptor type II has a significantly improved effect in the prevention of acute hepatic failure as compared with the conventional soluble TNFα receptor type II.

EXAMPLE 3

Prevention of Acute (Fulminant) Hepatic Failure in Mice Using Long-acting Recombinant Human Soluble Tumor Necrosis Factor (TNF) α Receptor (LHusTNFR) Type II in the Form of HusTNFR Type II-Human Serum Albumin Fulminant hepatic failure was induced via subcutaneous injection of either D-aminogalactose/endotoxin (GaIN/LPS) or Con-A (T cell mitogens concanavalin A) in mice. The mortality measure after 48 hrs was 80% and 50%, respectively. The gross specimen of liver exhibited severe congestion and intumesce. HE-staining of the pathological section showed massive severe hepatocyte necrosis.

In the group of prevention using the long-acting receptor of type II, C57BL/6 mice (GaIN/LPS sub-group) and BALB/c mice (Con-A sub-group) were subcutaneously injected with 5-30 mg/kg of the LHusTNFR type II prepared as described above (i.e., the fusion protein of LHusTNFR type II-human serum albumin prepared according to the method in paragraph (6) above, used as a prophylactic agent). The C57BL/6 mice (GaIN/LPS sub-group)and the BALB/c mice (Con-A sub-group) in the group of prevention using the conventional receptor of type II were subcutaneously injected with 12.5 mg/kg of the conventional HusTNFR. The same animals in the control group were subcutaneously injected with saline at the same volume, 16 hrs later, the prevention groups and the control group were subcutaneously injected with GaIN/LPS or Con-A. The mortality after 48 hrs was observed to be 80% in the GaIN/LPS sub-group in the control group (50% in the Con-A sub-group), 50% in the prevention group using the conventional receptor type II (30% for Con-A sub-group), 0% for prevention group using the long-acting receptor of type II (0% for Con-A sub-group). In the prevention group using the long-acting receptor of type II, the pathology examination showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type II (GaIN/LPS sub-group) were significantly decreased by 30-60%, as compared with the prevention group using the conventional receptor type II and the control group. And, the NF-kB level was decreased by 60% and 32% respectively in the comparison. The above results indicate that the TNFR type II-human serum albumin can block the signaling to the nucleus mediated by TNFα binding to the type II receptor on the hepatic cell membrane by inhibiting the binding of TNFα to the membrane receptor, and thus prevent the hepatocytic necrosis and the necrosis-associated acute hepatic failure. The results also indicate that the long-acting soluble TNFαreceptor type II has a significantly improved effect in the prevention of acute hepatic failure as compared with the conventional soluble TNFαreceptor type II.

EXAMPLE 4

Prevention of Sub-acute Hepatic Failure in Rats Using Long-acting Recombinant Human Soluble Tumor Necrosis Factor (TNF) αReceptor (LHusTNFR) Type I in the Form of HusTNFR Type I-IgG1:Fc Sub-acute hepatic failure was induced via subcutaneous injection with D-aminogalactose/endotoxin (GaIN/LPS) in the rats. The mortality after one week was 60%. The gross specimen of liver exhibited severe congestion and intumesce. The HE-staining of the pathological section showed a massive severe hepatocyte necrosis.

In the prevention group using the long-acting receptor type I, the Spraque-Dawley rats were subcutaneously injected with 12.5 mg/kg of the type I LHusTNFR prepared according to the present invention (i.e., the fusion protein of LHusTNFR type I-IgG1:Fc prepared according to the method in paragraph (1) above, used as a prophylactic agent). The Spraque-Dawley rats in the group of prevention using the conventional receptor type I were subcutaneously injected with 12.5 mg/kg of the conventional HusTNFR. The same animals in the control group were subcutaneously injected with saline at the same volume. 16 hrs later, the prevention groups and the control group were subcutaneously injected with GaIN/LPS. After one week, the mortality was observed to be 60% in the control group, 44% in the prevention group using the conventional receptor type I, and 0% in the prevention group using the long-acting receptor type I. In the prevention group using the long-acting receptor type I, the pathology examinatin showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type I were decreased by 90.5%, 78.1% and 84.3% as compared with the prevention group using the conventional receptor type I, and 46.7%, 52.2% and 37.8% as compared with the control group. And, the NF-kB level was decreased by 87.4% and 37.5% respectively in the comparison. The above results indicate that the soluble TNFαreceptor type I can block the signaling to nucleus mediated by the TNFαbinding to the receptor of type I on the hepatic cell membrane by inhibiting the binding of TNFα to the membrane receptor, and thus prevent the hepatocytic necrosis and the necrosis-associated acute hepatic failure. The results also indicate that the long-acting soluble TNFα receptor type I has a significantly improved effect in the prevention of sub-acute hepatic failure as compared with the conventional soluble TNFα receptor type I.

EXAMPLE 5

Prevention of Sub-acute Hepatic Failure in Rats Using Long-acting Recombinant Human Soluble Tumor Necrosis Factor (TNF) αReceptor (LHusTNFR) Type II in the Form of HusTNFR Type II-IgG1:Fc Sub-acute hepatic failure was induced via subcutaneous injection with D-aminogalactose/endotoxin (GaIN/LPS) in the rats. The mortality after one week was 60%. The gross specimen of liver exhibited severe congestion and intumesce. The HE-staining of the pathological section showed a massive severe hepatocyte necrosis.

In the prevention group using the long-acting receptor type II, the Spraque-Dawley rats were subcutaneously injected with 12.5 mg/kg of the type II LHusTNFR prepared according to the present invention (i.e., the fusion protein of LHusTNFR type II-IgG1:Fc prepared according to the method in paragraph (2) above, used as a prophylactic agent). The Spraque-Dawley rats in the group of prevention using the conventional receptor type II were subcutaneously injected with 12.5 mg/kg of the conventional HusTNFR. The same animals in the control group were subcutaneously injected with saline at the same volume. 16 hrs later, the prevention groups and the control group were subcutaneously injected with GaIN/LPS. After one week, the mortality was observed to be 60% in the control group, 44% in the prevention group using the conventional receptor type II, and 0% in the prevention group using the long-acting receptor type II. In the prevention group using the long-acting receptor type II, the pathology examinatin showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type II were decreased by 88.5%, 68.1% and 78.3% as compared with the prevention group using the conventional receptor type II, and 46.7%, 52.2% and 37.8% as compared with the control group. And, the NF-kB level was decreased by 92.1% and 37.5% respectively in the comparison. The above results indicate that the soluble TNFαreceptor type II can block the signaling to nucleus mediated by the TNFαbinding to the receptor of type II on the hepatic cell membrane by inhibiting the binding of TNFα to the membrane receptor, and thus prevent the hepatocytic necrosis and the necrosis-associated sub-acute hepatic failure. The results also indicate that the long-acting soluble TNFαreceptor type II has a significantly improved effect in the prevention of sub-acute hepatic failure as compared with the conventional soluble TNFα receptor type II.

EXAMPLE 6

Prevention of Sub-acute Hepatic Failure in Rats Using Long-acting Recombinant Human Soluble Tumor Necrosis Factor (TNF) αReceptor (LHusTNFR) Type II in the Form of HusTNFR type II-Human Serum Albumin Sub-acute hepatic failure was induced via subcutaneous injection with D-aminogalactose/endotoxin (GaIN/LPS) in the rats. The mortality after one week was 60%. The gross specimen of liver exhibited severe congestion and intumesce. The HE-staining of the pathological section showed a massive severe hepatocyte necrosis.

In the prevention group using the long-acting receptor type II, the Sprague-Dawley rats were subcutaneously injected with 5-30 mg/kg of the type II LHusTNFR prepared according to the present invention (i.e., the fusion protein of LHusTNFR type II-human serum albumin prepared according to the method in paragraph (6) above, used as a prophylactic agent). The Sprague-Dawley rats in the group of prevention using the conventional receptor type II were subcutaneously injected with 12.5 mg/kg of the conventional HusTNFR. The same animals in the control group were subcutaneously injected with saline at the same volume. 16 hrs later, the prevention groups and the control group were subcutaneously injected with GaIN/LPS. After one week, the mortality was observed to be 60% in the control group, 44% in the prevention group using the conventional receptor type II, and 0% in the prevention group using the long-acting receptor type II. In the prevention group using the long-acting receptor type II, the pathology examinatin showed mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. NF-kB level was measured by EMSA. The results showed that IL-6, MIP-2 and bcl-xL mRNA levels in the prevention group using the long-acting receptor type II were significantly decreased by 25-55% as compared with the prevention group using the conventional receptor type II and the control group. And, the NF-kB level was decreased by 51% and 27% respectively in the comparison. The above results indicate that the soluble TNFαreceptor type II can block the signaling to nucleus mediated by the TNFαbinding to the receptor of type II on the hepatic cell membrane by inhibiting the binding of TNFαto the membrane receptor, and thus prevent the hepatocytic necrosis and the necrosis-associated sub-acute hepatic failure. The results also indicate that the long-acting soluble TNFα receptor type II has a significantly improved effect in the prevention of sub-acute hepatic failure as compared with the conventional soluble TNFαreceptor type II.

EXAMPLE 7

Treatment of Sub-acute Hepatic Failure in Rats Using Long-acting Recombinant Human Soluble Tumor Necrosis Factor (TNF) Preceptor (LHusTNFR) Type I in the Form of HusTNFR Type I-IgG1:Fc Sub-acute hepatic failure was induced via subcutaneous injection with D-aminogalactose/endotoxin (GaIN/LPS). The mortality after one week was 60%. The specimen of liver exhibited severe congestion and intumesce. The HE-staining of the pathological section showed a massive severe hepatocyte necrosis.

The rat model of sub-acute hepatic failure was made by subcutaneous injection with GaIN/LPS. After 8 hrs, in the group treated with long-acting receptor of type I, the Spraque-Dawley rates were subcutaneously injected with 12.5 mg/kg of LHusTNFR type I prepared according to the present invention (i.e., the fusion protein of LHusTNFR type I-IgG1:Fc produced according to the method in paragraph (1)). The Spraque-Dawley rats in the group treated with the conventional receptor of type I were subcutaneously injected with 12.5 mg/kg of the conventional HusTNFR. The same animals in the control group were subcutaneously injected with saline at the same volume. The rats were observed for one week. Within one week post GaIN/LPS injection, the mortality was observed to be 60% in the control group, 30% in the group treated with the conventional receptor type I, 0% in the group treated with the long-acting receptor type I. In the group of treated with the long-acting receptor type I, the pathology examination showed only mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. The NF-kB level was measured by EMSA. The results showed that IL-6, MIP-2 and bcl-xL mRNA levels in the group treated with the long-acting receptor type I were decreased by 90.5%, 78.1% and 84.3% as compared with the group treated with the conventional receptor type I, and 46.7%, 52.2% and 37.8% as compared with the control group. And, the NF-kB level was decreased by 87.4% and 37.5% respectively in the compasition. The results above indicate that the soluble TNFαreceptor type I can block the signaling to the nucleus mediated by TNFα binding to the type I receptor on the hepatic cell membrane by inhibiting the binding of TNFαto the membrane receptor, and thus prevent the hepatocytic necrosis and the necrosis-associated sub-acute hepatic failure. The results also indicates that the long-acting soluble TNFαreceptor type I has a significantly improved effect in the treatment of sub-acute hepatic failure as compared with the conventional soluble TNFαreceptor type I.

EXAMPLE 8

Treatment of Sub-acute Hepatic Failure In Rats Using Long-acting Recombinant Human Soluble Tumor Necrosis Factor (TNF) αReceptor (LHusTNFR) Type II in the Form of HusTNFR Type II-IgG1:Fc Sub-acute hepatic failure was induced via subcutaneous injection with D-aminogalactose/endotoxin (GaIN/LPS). The mortality after one week was 60%. The specimen of liver exhibited severe congestion and intumesce. The HE-staining of the pathological section showed a massive severe hepatocyte necrosis.

The rat model of sub-acute hepatic failure was made by subcutaneous injection with GaIN/LPS. After 8 hrs, in the group treated with long-acting receptor of type II, the Spraque-Dawley rates were subcutaneously injected with 12.5 mg/kg of LHusTNFR type II prepared according to the present invention (i.e., the fusion protein of LHusTNFR type II-IgG1:Fc produced according to the method in paragraph (2)). The Spraque-Dawley rats in the group treated with the conventional receptor of type II were subcutaneously injected with 12.5 mg/kg of the conventional HusTNFR. The same animals in the control group were subcutaneously injected with saline at the same volume. The rats were observed for one week. Within one week post GaIN/LPS injection, the mortality was observed to be 60% in the control group, 30% in the group treated with the conventional receptor type II, 0% in the group treated with the long-acting receptor type II. In the group of treated with the long-acting receptor type II, the pathology examination showed only mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. The NF-kB level was measured by EMSA. The results showed that IL-6, MIP-2 and bcl-xL mRNA levels in the group treated with the long-acting receptor type II were decreased by 89%, 76% and 83% as compared with the group treated with the conventional receptor type II, and 44.3%, 49% and 35.2% as compared with the control group. And, the NF-kB level was decreased by 79.6% and 36% respectively in the compasition. The results above indicate that the soluble TNFαreceptor type II can block the signaling to the nucleus mediated by TNFα binding to the type II receptor on the hepatic cell membrane by inhibiting the binding of TNFαto the membrane receptor, and thus prevent the hepatocytic necrosis and the necrosis-associated sub-acute hepatic failure. The results also indicates that the long-acting soluble TNFαreceptor type II has a significantly improved effect in the treatment of sub-acute hepatic failure as compared with the conventional soluble TNFαreceptor type II.

EXAMPLE 9

Treatment of Sub-acute Hepatic Failure in Rats Using Long-acting Recombinant Human Soluble Tumor Necrosis Factor (TNF) αReceptor (LHusTNFR) Type II in the Form of HusTNFR Type II-Human Serum Albumin Sub-acute hepatic failure was induced via subcutaneous injection with D-aminogalactose/endotoxin (GaIN/LPS). The mortality after one week was 60%. The specimen of liver exhibited severe congestion and intumesce. The HE-staining of the pathological section showed a massive severe hepatocyte necrosis.

The rat model of sub-acute hepatic failure was made by subcutaneous injection with GaIN/LPS. After 8 hrs, in the group treated with long-acting receptor of type II, the Spraque-Dawley rates were subcutaneously injected with 5-30 mg/kg of LHusTNFR type II prepared according to the present invention (i.e., the fusion protein of LHusTNFR type II-human serum albumin produced according to the method in paragraph (6)). The Spraque-Dawley rats in the group treated with the conventional receptor of type II were subcutaneously injected with 12.5 mg/kg of the conventional HusT-NFR. The same animals in the control group were subcutaneously injected with saline at the same volume. The rats were observed for one week. Within one week post GaIN/LPS injection, the mortality was observed to be 60% in the control group, 30% in the group treated with the conventional receptor type II, 0% in the group treated with the long-acting receptor type II. In the group of treated with the long-acting receptor type II, the pathology examination showed only mild liver congestion and intumesce, the HE staining showed mild and spotty necrosis, and the massive hepatocyte necrosis as seen in the control group was not observed. The IL-6, MIP-2 and bcl-xL mRNA levels were measured by real-time PCR using the total RNAs and the nucleic proteins extracted from the liver. The NF-kB level was measured by EMSA. The results showed that IL-6, MIP-2 and bcl-xL mRNA levels in the group treated with the long-acting receptor type II were significantly decreased by 20-50% as compared with the group treated with the conventional receptor type II and the control group. And, the NF-kB level was decreased by 41% and 24% respectively in the compasition. The results above indicate that the soluble TNFαreceptor type II can block the signaling to the nucleus mediated by TNFα binding to the type II receptor on the hepatic cell membrane by inhibiting the binding of TNFαto the membrane receptor, and thus prevent the hepatocytic necrosis and the necrosis-associated sub-acute hepatic failure. The results also indicates that the long-acting soluble TNFαreceptor type II has a significantly improved effect in the treatment of sub-acute hepatic failure as compared with the conventional soluble TNFα receptor type II.

All references mentioned in this application are herein incorporated by reference into the specification to the same extent as if each was specifically and individually indicated to be incorporated herein by reference. Additionally, it will be understood that in light of the above disclosure of the present invention, those skilled in the art can make various changes and modifications, all of which are falling in the scope of the claims of the present invention.

The invention claimed is:

1. A method of preventing acute or sub-acute hepatic failure in a subject that does not have acute or sub-acute hepatic failure, comprising:

administering to the subject that does not have acute or sub-acute hepatic failure a fusion protein of human tumor necrosis factor α receptor II with human IgG1:Fc fragment in an amount effective for preventing acute or sub-acute hepatic failure.

2. The method of claim 1, wherein the fusion protein has a sequence of SEQ ID NO: 2.

3. The method of claim 1, wherein administering to the subject comprises administering the amount of the fusion protein before administering a drug that is capable of inducing hepatic failure in the subject.

4. The method of claim 3, wherein the drug is at least one selected from the group consisting of D-aminogalactose, endotoxin and T cell mitrogens concanavalin A.

5. The method of claim 1, wherein the amount of the fusion protein is an amount effective for suppressing the expression of at least one protein selected from the group consisting of IL-6, TNF-α, MIP-2, bcl-xL and NF-κB.

* * * * *

SEQUENCE LISTING

<160> NUMBER OF SEQ ID NOS: 6

<210> SEQ ID NO 1
<211> LENGTH: 403
<212> TYPE: PRT
<213> ORGANISM: Homo sapiens
<220> FEATURE:
<221> NAME/KEY: MISC_FEATURE
<223> OTHER INFORMATION: fusion protein

<400> SEQUENCE: 1

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

-continued

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
 50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr Glu Pro Lys Ser Cys
                165                 170                 175

Asp Lys Thr His Thr Cys Pro Pro Cys Pro Ala Pro Glu Leu Leu Gly
            180                 185                 190

Gly Pro Ser Val Phe Leu Phe Pro Pro Lys Pro Lys Asp Thr Leu Met
        195                 200                 205

Ile Ser Arg Thr Pro Glu Val Thr Cys Val Val Val Asp Val Ser His
    210                 215                 220

Glu Asp Pro Glu Val Lys Phe Asn Trp Tyr Val Asp Gly Val Glu Val
225                 230                 235                 240

His Asn Ala Lys Thr Lys Pro Arg Glu Glu Gln Tyr Asn Ser Thr Tyr
                245                 250                 255

Arg Val Val Ser Val Leu Thr Val Leu His Gln Asp Trp Leu Asn Gly
            260                 265                 270

Lys Glu Tyr Lys Cys Lys Val Ser Asn Leu Ala Leu Pro Ala Pro Ile
        275                 280                 285

Glu Lys Thr Ile Ser Lys Ala Lys Gly Gln Pro Arg Glu Pro Gln Val
    290                 295                 300

Tyr Thr Leu Pro Pro Ser Arg Glu Glu Met Thr Lys Asn Gln Val Ser
305                 310                 315                 320

Leu Thr Cys Leu Val Lys Gly Phe Tyr Pro Ser Asp Ile Ala Val Glu
                325                 330                 335

Trp Glu Ser Asn Gly Gln Pro Glu Asn Asn Tyr Lys Thr Thr Pro Pro
            340                 345                 350

Val Leu Asp Ser Asp Gly Ser Phe Phe Leu Tyr Ser Lys Leu Thr Val
        355                 360                 365

Asp Lys Ser Arg Trp Gln Gln Gly Asn Val Phe Ser Cys Ser Val Met
    370                 375                 380

His Glu Ala Leu His Asn His Tyr Thr Gln Lys Ser Leu Ser Leu Ser
385                 390                 395                 400

Pro Gly Lys

<210> SEQ ID NO 2
<211> LENGTH: 467
<212> TYPE: PRT
<213> ORGANISM: artificial sequence
<220> FEATURE:
<221> NAME/KEY: MISC_FEATURE
<223> OTHER INFORMATION: fusion protein

```
<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Leu Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415
```

```
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 171
<212> TYPE: PRT
<213> ORGANISM: Homo sapiens

<400> SEQUENCE: 3

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 4
<211> LENGTH: 235
<212> TYPE: PRT
<213> ORGANISM: Homo sapiens

<400> SEQUENCE: 4

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95
```

```
Thr Cys Arg Pro Gly Trp Tyr Cys Ala Leu Ser Lys Gln Glu Gly Cys
             100                 105                 110

Arg Leu Cys Ala Pro Leu Arg Lys Cys Arg Pro Gly Phe Gly Val Ala
             115                 120                 125

Arg Pro Gly Thr Glu Thr Ser Asp Val Val Cys Lys Pro Cys Ala Pro
             130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                 165                 170                 175

Val Cys Thr Ser Thr Ser Pro Thr Arg Ser Met Ala Pro Gly Ala Val
             180                 185                 190

His Leu Pro Gln Pro Val Ser Thr Arg Ser Gln His Thr Gln Pro Thr
             195                 200                 205

Pro Glu Pro Ser Thr Ala Pro Ser Thr Ser Phe Leu Leu Pro Met Gly
             210                 215                 220

Pro Ser Pro Pro Ala Glu Gly Ser Thr Gly Asp
225                 230                 235
```

```
<210> SEQ ID NO 5
<211> LENGTH: 790
<212> TYPE: PRT
<213> ORGANISM: artificial sequence
<220> FEATURE:
<221> NAME/KEY: MISC_FEATURE
<223> OTHER INFORMATION: fusion protein

<400> SEQUENCE: 5

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
             20                  25                  30

Pro Gly Pro Gly Gln Asp Thr Asp Cys Arg Glu Cys Glu Ser Gly Ser
             35                  40                  45

Phe Thr Ala Ser Glu Asn His Leu Arg His Cys Leu Ser Cys Ser Lys
 50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                 85                  90                  95

Ser Glu Asn Leu Phe Gln Cys Phe Asn Cys Ser Leu Cys Leu Asn Gly
             100                 105                 110

Thr Val His Leu Ser Cys Gln Glu Lys Gln Asn Thr Val Cys Thr Cys
             115                 120                 125

His Ala Gly Phe Phe Leu Arg Glu Asn Glu Cys Val Ser Cys Ser Asn
             130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr Gly Gly Gly Gly Ser
                 165                 170                 175

Gly Gly Gly Gly Ser Met Lys Trp Val Thr Phe Ile Ser Leu Leu Phe
             180                 185                 190

Leu Phe Ser Ser Ala Tyr Ser Arg Gly Val Phe Arg Arg Asp Ala His
             195                 200                 205

Lys Ser Glu Val Ala His Arg Phe Lys Asp Leu Gly Glu Glu Asn Phe
             210                 215                 220
```

```
Lys Ala Leu Val Leu Ile Ala Phe Ala Gln Tyr Leu Gln Gln Cys Pro
225                 230                 235                 240

Phe Glu Asp His Val Lys Leu Val Asn Glu Val Thr Glu Phe Ala Lys
            245                 250                 255

Thr Cys Val Ala Asp Glu Ser Ala Glu Asn Cys Asp Lys Ser Leu His
        260                 265                 270

Thr Leu Phe Gly Asp Lys Leu Cys Thr Val Ala Thr Leu Arg Glu Thr
    275                 280                 285

Tyr Gly Glu Met Ala Asp Cys Cys Ala Lys Gln Glu Pro Glu Arg Asn
290                 295                 300

Glu Cys Phe Leu Gln His Lys Asp Asp Asn Pro Asn Leu Pro Arg Leu
305                 310                 315                 320

Val Arg Pro Glu Val Asp Val Met Cys Thr Ala Phe His Asp Asn Glu
            325                 330                 335

Glu Thr Phe Leu Lys Lys Tyr Leu Tyr Glu Ile Ala Arg Arg His Pro
        340                 345                 350

Tyr Phe Tyr Ala Pro Glu Leu Leu Phe Phe Ala Lys Arg Tyr Lys Ala
    355                 360                 365

Ala Phe Thr Glu Cys Cys Gln Ala Ala Asp Lys Ala Ala Cys Leu Leu
370                 375                 380

Pro Lys Leu Asp Glu Leu Arg Asp Glu Gly Lys Ala Ser Ser Ala Lys
385                 390                 395                 400

Gln Arg Leu Lys Cys Ala Ser Leu Gln Lys Phe Gly Glu Arg Ala Phe
            405                 410                 415

Lys Ala Trp Ala Val Ala Arg Leu Ser Gln Arg Phe Pro Lys Ala Glu
        420                 425                 430

Phe Ala Glu Val Ser Lys Leu Val Thr Asp Leu Thr Lys Val His Thr
    435                 440                 445

Glu Cys Cys His Gly Asp Leu Leu Glu Cys Ala Asp Asp Arg Ala Asp
450                 455                 460

Leu Ala Lys Tyr Ile Cys Glu Asn Gln Asp Ser Ile Ser Ser Lys Leu
465                 470                 475                 480

Lys Glu Cys Cys Glu Lys Pro Leu Leu Glu Lys Ser His Cys Ile Ala
            485                 490                 495

Glu Val Glu Asn Asp Glu Met Pro Ala Asp Leu Pro Ser Leu Ala Ala
        500                 505                 510

Asp Phe Val Glu Ser Lys Asp Val Cys Lys Asn Tyr Ala Glu Ala Lys
    515                 520                 525

Asp Val Phe Leu Gly Met Phe Leu Tyr Glu Tyr Ala Arg Arg His Pro
530                 535                 540

Asp Tyr Ser Val Val Leu Leu Leu Arg Leu Ala Lys Thr Tyr Glu Thr
545                 550                 555                 560

Thr Leu Glu Lys Cys Cys Ala Ala Ala Asp Pro His Glu Cys Tyr Ala
            565                 570                 575

Lys Val Phe Asp Glu Phe Lys Pro Leu Val Glu Glu Pro Gln Asn Leu
        580                 585                 590

Ile Lys Gln Asn Cys Glu Leu Phe Glu Gln Leu Gly Glu Tyr Lys Phe
    595                 600                 605

Gln Asn Ala Leu Leu Val Arg Tyr Thr Lys Lys Val Pro Gln Val Ser
610                 615                 620

Thr Pro Thr Leu Val Glu Val Ser Arg Asn Leu Gly Lys Val Gly Ser
625                 630                 635                 640

Lys Cys Cys Lys His Pro Glu Ala Lys Arg Met Pro Cys Ala Glu Asp
            645                 650                 655
```

Tyr Leu Ser Val Val Leu Asn Gln Leu Cys Val Leu His Glu Lys Thr
            660                 665                 670

Pro Val Ser Asp Arg Val Thr Lys Cys Cys Thr Glu Ser Leu Val Asn
            675                 680                 685

Arg Arg Pro Cys Phe Ser Ala Leu Glu Val Asp Glu Thr Tyr Val Pro
690                 695                 700

Lys Glu Phe Asn Ala Glu Thr Phe Thr Phe His Ala Asp Ile Cys Thr
705                 710                 715                 720

Leu Ser Glu Lys Glu Arg Gln Ile Lys Lys Gln Thr Ala Leu Val Glu
            725                 730                 735

Leu Val Lys His Lys Pro Lys Ala Thr Lys Glu Gln Leu Lys Ala Val
            740                 745                 750

Met Asp Asp Phe Ala Ala Phe Val Glu Lys Cys Cys Lys Ala Asp Asp
            755                 760                 765

Lys Glu Thr Cys Phe Ala Glu Glu Gly Lys Lys Leu Val Ala Ala Ser
            770                 775                 780

Gln Ala Ala Leu Gly Leu
785                 790

<210> SEQ ID NO 6
<211> LENGTH: 854
<212> TYPE: PRT
<213> ORGANISM: artificial sequence
<220> FEATURE:
<221> NAME/KEY: MISC_FEATURE
<223> OTHER INFORMATION: fusion protein

<400> SEQUENCE: 6

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
            35                  40                  45

Ser Asp Thr Val Cys Asp Ser Cys Glu Asp Ser Thr Tyr Thr Gln Leu
        50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
            115                 120                 125

Arg Pro Gly Thr Glu Thr Ser Asp Val Val Cys Lys Pro Cys Ala Pro
        130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

```
Pro Ser Pro Pro Ala Glu Gly Ser Thr Gly Asp Gly Gly Gly Ser
225                 230                 235                 240

Gly Gly Gly Gly Ser Met Lys Trp Val Thr Phe Ile Ser Leu Leu Phe
                245                 250                 255

Leu Phe Ser Ser Ala Tyr Ser Arg Gly Val Phe Arg Arg Asp Ala His
            260                 265                 270

Lys Ser Glu Val Ala His Arg Phe Lys Asp Leu Gly Glu Glu Asn Phe
        275                 280                 285

Lys Ala Leu Val Leu Ile Ala Phe Ala Gln Tyr Leu Gln Gln Cys Pro
    290                 295                 300

Phe Glu Asp His Val Lys Leu Val Asn Glu Val Thr Glu Phe Ala Lys
305                 310                 315                 320

Thr Cys Val Ala Asp Glu Ser Ala Glu Asn Cys Asp Lys Ser Leu His
                325                 330                 335

Thr Leu Phe Gly Asp Lys Leu Cys Thr Val Ala Thr Leu Arg Glu Thr
            340                 345                 350

Tyr Gly Glu Met Ala Asp Cys Cys Ala Lys Gln Glu Pro Glu Arg Asn
        355                 360                 365

Glu Cys Phe Leu Gln His Lys Asp Asp Asn Pro Asn Leu Pro Arg Leu
    370                 375                 380

Val Arg Pro Glu Val Asp Val Met Cys Thr Ala Phe His Asp Asn Glu
385                 390                 395                 400

Glu Thr Phe Leu Lys Lys Tyr Leu Tyr Glu Ile Ala Arg Arg His Pro
                405                 410                 415

Tyr Phe Tyr Ala Pro Glu Leu Leu Phe Phe Ala Lys Arg Tyr Lys Ala
            420                 425                 430

Ala Phe Thr Glu Cys Cys Gln Ala Ala Asp Lys Ala Ala Cys Leu Leu
        435                 440                 445

Pro Lys Leu Asp Glu Leu Arg Asp Glu Gly Lys Ala Ser Ser Ala Lys
    450                 455                 460

Gln Arg Leu Lys Cys Ala Ser Leu Gln Lys Phe Gly Glu Arg Ala Phe
465                 470                 475                 480

Lys Ala Trp Ala Val Ala Arg Leu Ser Gln Arg Phe Pro Lys Ala Glu
                485                 490                 495

Phe Ala Glu Val Ser Lys Leu Val Thr Asp Leu Thr Lys Val His Thr
            500                 505                 510

Glu Cys Cys His Gly Asp Leu Leu Glu Cys Ala Asp Asp Arg Ala Asp
        515                 520                 525

Leu Ala Lys Tyr Ile Cys Glu Asn Gln Asp Ser Ile Ser Ser Lys Leu
    530                 535                 540

Lys Glu Cys Cys Glu Lys Pro Leu Leu Glu Lys Ser His Cys Ile Ala
545                 550                 555                 560

Glu Val Glu Asn Asp Glu Met Pro Ala Asp Leu Pro Ser Leu Ala Ala
                565                 570                 575

Asp Phe Val Glu Ser Lys Asp Val Cys Lys Asn Tyr Ala Glu Ala Lys
            580                 585                 590

Asp Val Phe Leu Gly Met Phe Leu Tyr Glu Tyr Ala Arg Arg His Pro
        595                 600                 605

Asp Tyr Ser Val Val Leu Leu Leu Arg Leu Ala Lys Thr Tyr Glu Thr
    610                 615                 620

Thr Leu Glu Lys Cys Cys Ala Ala Ala Asp Pro His Glu Cys Tyr Ala
625                 630                 635                 640

Lys Val Phe Asp Glu Phe Lys Pro Leu Val Glu Glu Pro Gln Asn Leu
```

-continued

```
                      645                 650                 655
Ile Lys Gln Asn Cys Glu Leu Phe Glu Gln Leu Gly Glu Tyr Lys Phe
            660                 665                 670

Gln Asn Ala Leu Leu Val Arg Tyr Thr Lys Lys Val Pro Gln Val Ser
            675                 680                 685

Thr Pro Thr Leu Val Glu Val Ser Arg Asn Leu Gly Lys Val Gly Ser
            690                 695                 700

Lys Cys Cys Lys His Pro Glu Ala Lys Arg Met Pro Cys Ala Glu Asp
705                 710                 715                 720

Tyr Leu Ser Val Val Leu Asn Gln Leu Cys Val Leu His Glu Lys Thr
                    725                 730                 735

Pro Val Ser Asp Arg Val Thr Lys Cys Cys Thr Glu Ser Leu Val Asn
                    740                 745                 750

Arg Arg Pro Cys Phe Ser Ala Leu Glu Val Asp Glu Thr Tyr Val Pro
            755                 760                 765

Lys Glu Phe Asn Ala Glu Thr Phe Thr Phe His Ala Asp Ile Cys Thr
            770                 775                 780

Leu Ser Glu Lys Glu Arg Gln Ile Lys Lys Gln Thr Ala Leu Val Glu
785                 790                 795                 800

Leu Val Lys His Lys Pro Lys Ala Thr Lys Glu Gln Leu Lys Ala Val
                805                 810                 815

Met Asp Asp Phe Ala Ala Phe Val Glu Lys Cys Cys Lys Ala Asp Asp
                820                 825                 830

Lys Glu Thr Cys Phe Ala Glu Glu Gly Lys Lys Leu Val Ala Ala Ser
            835                 840                 845

Gln Ala Ala Leu Gly Leu
850
```